United States Patent [19]
Hasenzahl et al.

[11] Patent Number: 5,919,430
[45] Date of Patent: Jul. 6, 1999

[54] PREPARATION OF CRYSTALLINE MICROPOROUS AND MESOPOROUS METAL SILICATES, PRODUCTS PRODUCED THEREBY AND USE THEREOF

[75] Inventors: Steffen Hasenzahl, Hanau; Helmut Mangold, Rodenbach; Eckehart Roland, Bruchköbel; Mario Scholz, Gründau; Georg Thiele, Hanau, all of Germany

[73] Assignee: Degussa Aktiengesellschaft, Frankfurt Am Main, Germany

[21] Appl. No.: 08/878,509

[22] Filed: Jun. 19, 1997

Related U.S. Application Data

[60] Provisional application No. 60/029,676, Oct. 30, 1996.

[30] Foreign Application Priority Data

Jun. 19, 1996 [DE] Germany ............... 196 24 340

[51] Int. Cl.$^6$ ............ C01B 39/04; C01B 39/36; C01B 39/48
[52] U.S. Cl. ............ 423/702; 423/705; 423/707; 423/713; 423/716; 423/DIG. 22; 423/DIG. 27; 423/DIG. 29; 423/326; 423/328.2
[58] Field of Search ............... 423/326, 328.2, 423/702, 704, 705, 707, 713, 712, 716, 717, DIG. 22, DIG. 27, DIG. 29

[56] References Cited

U.S. PATENT DOCUMENTS

| | | | |
|---|---|---|---|
| 3,472,617 | 10/1969 | McDaniel et al. | 423/716 |
| 4,853,203 | 8/1989 | Guth et al. | 423/708 |
| 4,861,571 | 8/1989 | Harada et al. | 423/716 |
| 5,460,796 | 10/1995 | Verduijn | 423/716 |
| 5,558,851 | 9/1996 | Miller | 423/716 |
| 5,589,153 | 12/1996 | Garces et al. | 423/705 |
| 5,688,484 | 11/1997 | Saxton et al. | 423/700 |
| 5,716,593 | 2/1998 | Miller | 423/716 |
| 5,785,944 | 7/1998 | Miller | 423/716 |
| 5,785,945 | 7/1998 | Miller | 423/716 |

FOREIGN PATENT DOCUMENTS

| | | |
|---|---|---|
| 0311 983 | 10/1987 | European Pat. Off. . |
| 0299430 | 1/1989 | European Pat. Off. . |
| 0292363 | 4/1989 | European Pat. Off. . |
| 0543247 | 5/1993 | European Pat. Off. . |
| 2582639 | 12/1986 | France . |
| 30 21 580 | 12/1981 | Germany . |
| 30 31 557 | 3/1982 | Germany . |

*Primary Examiner*—Mark L. Bell
*Assistant Examiner*—David Sample
*Attorney, Agent, or Firm*—Smith, Gambrell & Russell, LLP; Beveridge, DeGrandi, Weilacher & Young Intellectual Property Group

[57] ABSTRACT

Microporous and mesoporous metal silicates are prepared by the hydrothermal reaction of a silicon and metal source in the presence of a template. The choice of raw materials influences the purity and hence the catalytic activity of the products. A pyrogenic mixed oxide is used as the silicon and metal source. Prepared products have the composition $(SiO_2)_{1-x}(A_mO_n)_x$, where A is Ti, Al, B, V or Zr and x is 0.005 to 0.1. Shaped objects of the microporous and mesoporous metal silicates are obtained directly by using a shaped object of the pyrogenic mixed oxide. The products obtained are used as oxidation catalysts.

20 Claims, No Drawings

PREPARATION OF CRYSTALLINE MICROPOROUS AND MESOPOROUS METAL SILICATES, PRODUCTS PRODUCED THEREBY AND USE THEREOF

This application is based upon and claims priority of U.S. provisional application Ser. No. 60/029,676, filed on Oct. 30, 1996.

INTRODUCTION AND BACKGROUND

The present invention relates to a process for the preparation of crystalline microporous and mesoporous metal silicates composed of silicon dioxide and one or more metal oxides. In another aspect, the present invention relates to products obtainable by said process. Still further, the present invention relates to the use of these products.

A variety of crystalline microporous and mesoporous metal silicates are known. According to the IUPAC definition, micropores are understood as meaning pores with a diameter of less than 2 nm, and mesopores are understood as meaning pores with a diameter of 2 to 50 nm. These definitions are used herein.

Some crystalline metal silicates with regular micropores or mesopores are extremely effective catalysts in a very wide variety of applications. In particular, microporous products of the composition $(SiO_2)_{1-x}(TiO_2)_x$, in which titanium atoms replace some of the silicon atoms in the crystal lattice, have achieved industrial importance as oxidation catalysts. The structures of these metal silicates differ according to the starting materials and conditions of preparation. Thus, for example, so-called titanium silicalite-1, titanium silicalite-2 and titanium beta-zeolite have the MFI, MEL and BEA crystal structures, respectively. Crystal structure types of known zeolites and silicalites are described in W. M. Meier, D. H. Olson, *Atlas of Zeolite Structure Types*, Butterworth-Heinemann, 1993. Known structures with regular mesopores are the MCM-41 and MCM-48 structures described in C. T. Kresge et al., *Nature*, 359 (1992), pp. 710–712. A survey of structures with regular mesopores is also given in S. Behrens, *Angew, Chemie*, 1996, 108 (5), pp. 561–564.

It is known that the catalytic efficacy of generic metal silicates is substantially dependent on their phase purity and the morphology and, hence, on the conditions of preparation. For example, the catalytic activity of titanium silicalite is reduced by other titanium-containing phases, for instance $TiO_2$, and by an increase in the crystal size; see, B. Notari in (a) *Catal. Today* 18 (1993), p. 163 and (b) *Stud. Surf. Sci. Catal.*, 67 (1991), p. 243.

Generic metal silicates, for instance titanium silicalite-1, can be prepared by hydrothermal synthesis. In the first step, a silicon source and a titanium source, conventionally tetraalkyl orthosilicate and tetraalkyl orthotitanate, and water are condensed to a gel in the presence of a structure-determining quaternary ammonium cation, usually used in the form of the quaternary ammonium hydroxide, and the gel is then crystallized under hydrothermal conditions, usually above 100° C. and under autogenous pressure. The solid that is form is separated off, washed, dried and calcined above 300° C. The way in which the Ti component is introduced is liable to cause problems, it often being impossible to exclude contamination of the product by $TiO_2$ as a foreign phase—loc. cit. B. Notari (b). According to EP 543 247, the quaternary ammonium hydroxide can be replaced as the template with a combination of a quaternary ammonium salt and a base such as ammonia, although the crystals obtained are relatively large. According to U.S. Pat. No. 5,198,203 a mesoporous titanium silicate of the MCM-41 structure can be prepared with cetyltrimethylammonium hydroxide as the template.

Another known silicon source is pyrogenic silicic acid. According to R. Kumar et al. in *Stud. Surf. Sci. Catal.*, 84 (1994) p. 109, titanium silicalite-1 can be obtained by hydrothermal synthesis from pyrogenic silicic acid and tetrabutyl orthotitanate. The use of a tetraalkyl orthotitanate carries the risk of obtaining a product of insufficient phase purity.

According to EP 0 311 983, titanium silicalites are prepared by impregnating a coprecipitated porous $TiO_2$—$SiO_2$ material, which can be amorphous or crystalline, with a template compound and then subjecting the product to hydrothermal synthesis. Suggestions of using coprecipitates with other metals, or pyrogenic mixed oxides, are not to be found in said document.

In known synthesis processes the generic microporous metal silicates are formed as crystallites with a size usually of less than one micrometer, which can only be separated from a liquid at considerable expenses. For many industrial applications the fine material is therefore coarsened by a subsequent agglomeration step. According to EP 0 265 018, the agglomeration is effected using oligomeric $SiO_2$ as a binder.

According to EP 0 299 430, a preformed amorphus $SiO_2$ matrix is impregnated with an aqueous solution containing a soluble titanium compound and a suitable template, and crystallized under hydrothermal conditions, the shape and size of the $SiO_2$ matrix remaining essentially unchanged. This process again has the disadvantage that the use of a soluble titanium compound carries the risk of reducing the phase purity and hence the catalytic activity.

Accordingly, it is an object of the invention to produce generic metal silicates of high phase purity and high catalytic activity.

Another object of the invention is to provide a process suitable not only for the preparation of products based on $(SiO_2)_{1-x}(TiO_2)_x$, but also for the preparation of products in which titanium is replaced with one or more other metals in the crystal lattice.

Still further, another object of the invention is to carry out the process in such a way that binder-free shaped objects of the crystalline microporous and mesoporous metal silicates can be obtained directly, i.e., without a subsequent agglomeration step.

SUMMARY OF THE INVENTION

In achieving the above and other objects, a feature of the invention resides in a process for the preparation of microporous and mesoporous metal silicates, comprising the hydrothermal reaction of a silicon source in the presence of a metal source and a template wherein a pyrogenic metal-silicon mixed oxide is used as the silicon and metal source. Any suitable template can be used for purposes of the invention.

DETAILED DESCRIPTION OF THE INVENTION

The general composition of the pyrogenic mixed oxides and hence also of the crystalline microporous and mesoporous metal silicates to be prepared is represented as follows:

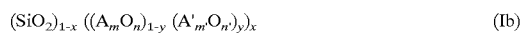

In the above formulae, A and A' are each the same or different metal of valency p selected from the group consisting of:

B, Al, Ga, In, Ge, Sn and Pb or from subgroups 3 to 8;

m and m' and n and n' are the number of atoms, where m·p=2n and m'·p=2n';

x is a number from 0.0001 to 0.25, preferably from 0.001 to 0.2 and especially from 0.005 to 0.1; and y in formula (Ib) is a number greater than 0 and less than 1.

Apart from $SiO_2$, pyrogenic mixed oxides which are preferably to be used contain one or more oxides selected from the group consisting of $Al_2O_3$, $B_2O_3$, $TiO_2$, $ZrO_2$, $V_2O_5$, $Cr_2O_3$ and $Fe_2O_3$. Oxides of the subgroup elements are optionally present not only in the highest oxidation state but also in a lower oxidation state. Generic metal silicates which are to be used as oxidation catalysts are prepared with mixed oxides which are free of aluminum oxide, the process according to the invention giving metal silicalites in this case. Generic metal silicates of the composition $$(SiO_2)_{1-x}(M_rA_mO_{n''})_x \qquad (II)$$

are prepared using mixed oxides of composition (Ia). M in composition (II) is a cation of valency q selected from the group consisting of alkali metals, alkaline earth metals, $H^+$, $NH_4^+$ and $N(alkyl)_4^+$; m·p+r·q=2n" in (II). In the process according to the invention, M is introduced into the metal silicate either via the template or via alkali metal or alkaline earth metal hydroxide or ammonia present in the hydrothermal synthesis. After the calcination of a generic metal silicate of composition (II), M is a proton or an alkali metal or alkaline earth metal ion. However, said cations M or other cations can also be incorporated into the microporous and mesoporous metal silicates at a later stage by means of conventional ion exchange reactions.

The pyrogenic mixed oxides to be used in the process according to the invention can be prepared in a manner known per se from a mixture of a volatile silicon compound and one or more volatile metal compounds (compounds of A and/or A'), for example, by flame hydrolysis or the luminous arc process. The process according to the invention is preferably carried out using pyrogenic mixed oxides of silicon which have been prepared by flame hydrolysis, for example, those known from Ullmann's *Encyklopädie der Technischen Chemie* (Ullmann's *Encyclopedia of Chemical Technology*), 4th edition, vol. 21, pp. 464–465 (1982) and DE-A 36 11 449.

The process according to the invention can be carried out using both the pulverulent pyrogenic mixed oxides and shaped objects thereof.

The shaped objects of the metal-silicon mixed oxide can be produced by known processes, for example, spray granulation, fluidized bed granulation, extrusion, pelleting or tableting. In a preferred embodiment of the invention the shaped objects can be produced by means of spray granulation, as described, for example, in DE-A 36 11 449.

In the process according to the invention the pyrogenic metal/silicon mixed oxide, in powder form or in the form of a binder-free shaped object produced therefrom, is brought into contact with an aqueous solution of a suitable template; when using coarser shaped objects of mixed oxide, for instance extrudates, this is conventionally an impregnation process. After intermediate drying, if appropriate, this step is followed by the hydrothermal reaction to convert the pyrogenic metal-silicon mixed oxide to the crystalline microporous or mesoporous metal silicate according to the invention. After the hydrothermal reaction, the template is removed from the metal silicate in a manner known, per se, conventionally by extraction or, preferably by calcination.

Suitable template compounds are amines having one or more amino groups, amino alcohols or tetrasubstituted ammonium compounds. Tetraalkylammonium compounds are particularly suitable, especially tetraalkylammonium hydroxide. The nature of the alkyl groups in said tetraalkylammonium compounds is significant in terms of the pore structure. The tetraalkylammonium compounds used to prepare microporous metal silicates according to the invention are preferably those in which alkyl is ethyl, propyl and butyl, preferably n-propyl. Thus, for example, metal silicates according to the invention of the MFI, MEL and BEA structure can be prepared using tetra-n-propylammonium, tetra-n-butylammonium and tetraalkylammonium compounds, respectively. The tetraalkylammonium compounds used to prepare mesoporous metal silicates according to the invention are preferably those which have surfactant properties. Accordingly, these compounds contain an alkyl group or an alkenyl group having at least 7 C atoms in the longest chain. Particularly preferred ammonium compounds are those of the general formula $RNR'_3{}^+X^-$, in which R contains 12 to 18 C atoms and is preferably unbranched and saturated, R' has 1 or 2 C atoms, and X is the anion, conventionally hydroxide or halide. Cetyltrimethylammonium chloride or bromide and lauryltrimethylammonium chloride or bromide are particularly suitable for the preparation of mesoporous structures. When using tetraalkylammonium halides as the template, a base, such as ammonia, a primary, secondary or tertiary amine or an alkali metal or alkaline earth metal hydroxide, is added to the template solution used for the contacting/impregnation process. The template compound is conventionally used in a molar ratio of template to $SiO_2$ of 0.05 to 2.0. For the preparation of microporous metal silicates, a molar ratio of template to $SiO_2$ from 0.05 to 1.0, especially from 0.10 to 0.45, is preferred. For the preparation of mesoporous metal silicates according to the invention of the MCM-41 or MCM-48 structure, a molar ratio of template to $SiO_2$ of from 0.05 to 2.0, especially of from 0.1 to 0.8, is preferred.

The molar ratio $OH^-/SiO_2$ is generally from 0.05 to 2.0 and preferably from 0.1 to 1.0. In the hydrothermal reaction to the molar ratio $H_2O/SiO_2$ is from 1 to 200 and preferably from 4 to 100. Seed crystals of the same structural type can be added to the reaction mixture if necessary. The molar ratio $H_2O/SiO_2$ is generally lower when using shaped objects of pyrogenic mixed oxides than when using pyrogenic mixed oxides as obtained directly by flame hydrolysis.

In the process according to the invention for the preparation of microporous metal silicates, the hydrothermal reaction is conventionally carried out under autogenous pressure at a temperature from 100 to 200° C. and preferably from 150 to 190° C. Mesoporous metal silicates according to the invention can also be prepared at lower temperature, the conventional temperature range being from 25 to 200° C., preferably from 50 to 175° C. and especially from 70 to 150° C. The hydrothermal reaction is carried out until the pyrogenic mixed oxide used has been completely converted to the crystalline microporous or mesoporous metal silicate according to the invention at the given reaction temperature. The degree of completion of the reaction can be determined by known methods of structural analysis. Under optimized conditions the reaction time is conventionally from 1 to 50 hours.

To remove the template compound from the solid obtained in the hydrothermal reaction, said solid is usually calcined at from 300 to 1000° C., optionally after a prior washing process, it being possible for the calcination step to include a shaping process at the same time. In the case of the mesoporous metal silicates according to the invention, at least some of the template compound can also be removed by extraction with an organic solvent.

In one particular embodiment of the process according to the invention, the pyrogenic metal-silicon mixed oxide, for instance as obtained by flame hydrolysis, is suspended in an aqueous template solution. The molar ratios used here can be the same as those indicated above. This suspension is spray-dried, and the resulting granules containing the template are treated in an autoclave at elevated temperature, for example, at 175° C., optionally in a steam atmosphere. The spray drying is advantageously carried out by setting the temperature of the drying air in the range of 100 to 500° C. so that the resulting granules have a water content of 5 to 50 wt. %. After the hydrothermal reaction, the shaped objects obtained are calcined at a temperature of 300 to 1000° C., preferably of 400 to 800° C., to remove the template.

The process according to the invention can be carried out reproducibly and is easy to control. The use of the pyrogenic mixed oxides avoids problems due to the presence of foreign phases of the metal oxides in question. A high catalytic activity is a characteristic feature of the crystalline microporous and mesoporous metal silicates obtainable by the process according to the invention. The generic metal silicates can moreover be obtained not only in the form of very finely powdered materials but also in the form of different shaped objects. When using shaped objects of pyrogenic mixed oxides or forming such shaped objects directly before the hydrothermal reaction, a subsequent agglomeration step is not necessary. The addition of catalytically inactive binders is also superfluous.

A further advantage of shaped objects of crystalline microporous and mesoporous metal silicates obtainable according to the invention is that they can be separated more easily from liquids by filtration than unshaped catalysts, thereby facilitating their use as suspension catalysts. As pyrogenic mixed oxides are easy to shape, for instance into spheres, extrudates, pellets or tablets and the shape remains essentially unchanged in the process according to the invention, said process directly produces suitable shaped objects for use as catalysts in fixed bed reactions.

Although it is know from EP 0 311 983 B that coprecipitated $TiO_2$—$SiO_2$ material can be used for the preparation of titanium silicates, the copreciptates to be used are very porous products. It was therefore surprising that crystalline microporous and mesoporous metal silicates are easily obtainable by using pore-free pyrogenic mixed oxides such as those used in the process according to the invention.

As such, preferably in the form of shaped objects, the crystalline microporous and mesoporous metal silicates obtainable according to the invention are used as catalysts. Titanium silicalites and other aluminum-free products are particularly suitable as catalysts for oxidation reactions with hydrogen peroxide or organic hydroperoxides. Examples are the use of titanium silicalite-1 as a catalyst for the reaction of olefins, i.e., propene, with hydrogen peroxide to give epoxides (EP 100 119), the reaction of aromatics with hydrogen peroxide to give hydroxyaromatics (DE 31 35 559), the reaction of aliphatic hydrocarbons with hydrogen peroxide to give alcohols and ketones (EP 376 453) and the reaction of cyclohexanone with hydrogen peroxide and ammonia to give cyclohexanone oxime (EP 208 311). Titanium silicalite-2 is used as a catalyst for the hydroxylation of phenol (J. S. Reddy, S. Sivasanker, P. Ratnasamy, *J. Mol. Catal.* 71 (1992) p. 373) and for the reaction of cyclohexanone with hydrogen peroxide and ammonia to give cyclohexanone oxime (J. S. Reddy, Reddy, S. Sivasanker, P. Ratnasamy, *J. Mol. Catal.* 71 (1992) p. 383). Titanium beta-zeolite can be used as a catalyst for the reaction of olefins with hydrogen peroxide or organic hydroperoxides to give epoxides (A. Corma, P. Esteve, A. Martinez, S. Valencia, *J. Catal.* 152 (1995) p. 18 and EP 659 685).

The following examples serve to illustrate the present invention.

EXAMPLE 1

Preparation of Titanium Silicalite-1 Powder 137.0 g of tetrapropylammonium hydroxide solution (40 wt. %) and 434.2 g of deionized water are placed in a polyethylene beaker and 111.1 g of pyrogenic silicon-titanium mixed oxide containing 3.0 wt. % of $TiO_2$ are added, with stirring. The resulting synthesis gel is first aged for four hours at 80° C., with stirring, and then crystallized in an autoclave for 24 hours at 175° C. The solid obtained is separated from the mother liquor by centrifugation, washed with three times 250 ml of deionized water, dried at 90° C. and calcined in an air atmosphere for four hours at 550° C. The yield is 98.3 g.

The X-ray diffraction diagram of the catalyst prepared in this way shows the diffraction pattern typical of the MFI structure, and the IR spectrum shows the band at 960 $cm^{-1}$ characteristic of titanium-containing molecular sieves. Wet chemical analysis gives a titanium content of 2.3 wt. % of $TiO_2$. The DR-UV-Vis spectrum also shows that the sample is free of titanium dioxide.

EXAMPLE 2

Application Example of the Epoxidation of Propylene With Hydrogen Peroxide 1.0 g of the catalyst prepared according to Example 1 in 300 ml of the methanol is placed in a thermostated laboratory autoclave with gas dispersion stirrer, at 40° C. under a propylene atmosphere, and the solvent is saturated with propylene under an excess pressure of 3 bar. 13.1 g of 30 wt. % aqueous hydrogen peroxide solution is then added all at once, with stirring, and the reaction mixture is kept at 40° C. and 3 bar, additional propylene being metered in via a pressure regulator in order to make up the quantity consumed by the reaction. Samples are taken at regular intervals via a filter, and hydrogen peroxide content of the reaction mixture is determined by redox titration with cerium (IV) sulphate solution. The plot of $ln(c/c_0)$ against the time t, c being the measured $H_2O_2$ concentration at time t and $c_0$ being the calculated $H_2O_2$ concentration at the start of the reaction, gives a straight line. An activity coefficient k of 25.4 $min^{-1}$ is determined from the gradient of the lines by means of the relationship $dc/dt=-k·c·c_{cat}$, where $c_{cat}$ is the catalyst concentration in kg of catalyst per kg of reaction mixture.

EXAMPLE 3

Preparation of Titanium Silicalite-1 Microgranules 800 g of deionized water and 30 g of acetic acid are placed in a polyethylene beaker and 200 g of pyrogenic silicon-titanium mixed oxide containing 3.6 wt. % of $TiO_2$ are added, with stirring. This mixture is sheared for five minutes in an Ultraturax stirrer. The resulting suspension is dried by means of a spray dryer (NIRO-Atomizer model 1638; inlet temperature 380° C.; outlet temperature 102° C.; speed of rotation of the spray disk 15,000 min$^{-1}$). 20 g of the resulting microgranules, with a mean particle diameter of 30 μm, are impregnated with a mixture of 20 g of tetrapropylammonium hydroxide solution (40 wt. %) and 20 g of deionized water. The impregnated microgranules are charged into an autoclave with a Teflon inliner and crystallized for 24 hours at 175° C. under static conditions. The solid obtained is separated from the mother liquor by centrifugation, washed three times with 100 ml of deionized water, dried at 90° C. and calcined in an air atmosphere for four hours at 550° C. The yield is 17 g.

The catalyst prepared in this way consists of titanium silicalite-1 microgranules.

EXAMPLE 4

Preparation of Titanium Silicalite-1 Microgranules 720.7 g of deionized water and 179.3 g of tetrapropylammonium hydroxide solution (40 wt. %) are placed in a polyethylene beaker and 100 g of pyrogenic silicon-titanium mixed oxide containing 3.6 wt. % of $TiO_2$ are added, with stirring. This mixture is sheared for five minutes in an Ultraturax stirrer. The resulting suspension is dried by means of a spray dryer (NIRO-Atomizer model 1638; inlet temperature 380° C.; outlet temperature 90° C.; speed of rotation of the spray disk 15,000 min$^{-1}$). 20 g of the resulting microgranules, with a mean particle diameter of 30 μm, a loss on drying of 23 wt. % (10 h at 105° C.; corresponds to the water content) and a loss on calcination of 43 wt. % (5 h at 550° C.; corresponds to the water and template content), are charged into an autoclave with a Teflon inliner and crystallized for 4 days at 180° C. under static conditions. The solid is then dried at 90° C. and calcined in an air atmosphere for four hours at 550° C.

The catalyst prepared in this way consists of titanium silicalite-1 microgranules.

EXAMPLE 5

Preparation of a Titanium Beta-Zeolite Powder 435.3 g of tetraethylammonium hydroxide solution (35 wt. %) and 236.3 g of deionized water are placed in a polyethylene beaker and 109.6 g of pyrogenic silicon-titanium mixed oxide containing 3.0 wt. % of $TiO_2$ is added. The resulting mixture is aged for four hours at 80° C. and, after cooling to room temperature, 12 g of beta-zeolite seed crystals with an $SiO_2/Al_2O_3$ ratio of 27 are added. This synthesis gel is crystallized in an autoclave for 3 days at 150° C., with stirring.

The solid obtained is separated from the mother liquor by centrifugation, washed three times, each time with 250 ml of deionized water, dried at 90° C. and calcined in an air atmosphere for four hours at 550° C.

The X-ray diffraction diagram of the catalyst prepared in this way shows the diffraction pattern typical of the BEA structure. Wet chemical analysis gives a titanium content of 1.8 wt. % of $TiO_2$.

EXAMPLE 6

Preparation of a Mesoporous Titanium Silicate of the MCM-41 Structure 114.2 of tetramethylammonium hydroxide solution (10% wt. %) is placed in a polyethylene beaker and 30.0 g of pyrogenic silicon-titanium mixed oxide containing 3.6 wt. % of $TiO_2$ are added, with stirring. This mixture is stirred for one hour. A suspension of 29.1 g of cetyltrimethylammonium bromide ($C_{16}H_{33}(CH_3)_3NBr$) in 109.2 g of deionized water is then added, with stirring, and stirring is continued for 10 minutes. The resulting synthesis gel (molar composition: $SiO_2$: 0.17 $C_{16}H_{33}(CH_3)_3N^+$: 0.26 $Me_4NOH$: 25 $H_2O$) is crystallized in an autoclave for 48 hours at 140° C. under static conditions. The solid obtained is filtered off and washed with deionized water until the filtrate is neutral. The solid is dried at 90° C. and then calcined in an air atmosphere for four hours at 640° C. The yield is 28 g.

The X-ray diffraction diagram of the catalyst prepared in this way shows the diffraction pattern typical of the MCM-41 materials, with $d_{100}$ reflection at 3.60 nm. Examination by sorption analysis with nitrogen at 77 K shows a mean pore diameter of 3.16 nm, a BET specific surface area of 1040 m$^2$ g$^{-1}$ and a pore volume of 0.89 ml/g. Wet chemical analysis gives a titanium content of 4.6 wt. % of $TiO_2$. The material is catalytically active in the epoxidation of propene with hydrogen peroxide.

EXAMPLE 7

Preparation of a Mesoporous Titanium Silicate of the MCM-48 Structure 114.2 g of tetramethylammonium hydroxide solution (10% wt. %) is placed in a polyethylene beaker and 30.0 g of pyrogenic silicon-titanium mixed oxide containing 3.6 wt. % of $TiO_2$ are added, with stirring. This mixture is stirred for one hour. A suspension of 114.2 g of cetyltrimethylammonium bromide ($C_{16}H_{33}(CH_3)_3NBr$) in 435.2 g of deionized water is then added, with stirring, and stirring is continued for 10 minutes. The resulting synthesis gel (molar composition: $SiO_2$: 0.65 $C_{16}H_{33}(CH_3)_3NBr$: 0.26 $Me_4NOH$: 62 $H_2O$) is crystallized in an autoclave for 48 hours at 140° C. under static conditions. The solid obtained is filtered off and washed with deionized water until the filtrate is neutral. The solid is dried at 90° C. and then calcined in an air atmosphere for four hours at 640° C.

The catalyst prepared in this way consists of Ti-MCM-48.

EXAMPLE 8

Preparation of a Boron Pentasil Zeolite 800 g of aqueous hexamethylenediamine solution (50 wt. %) is placed in a polyethylene beaker and 70.7 g of pyrogenic silicon-boron mixed oxide containing 9.5 wt. % of $B_2O_3$ is added, with stirring. This mixture is stirred for half an hour and then crystallized in an autoclave for five days at 170° C. The solid obtained is separated from the mother liquor by centrifugation, washed three times in 250 ml of deionized water, dried at 90° C. and calcined in an air atmosphere for six hours at 550° C.

The X-ray diffraction diagram of the catalyst prepared in this way shows the diffraction pattern typical of the MFI structure. Wet chemical analysis gives a $B_2O_3$ content of 2.4 wt. %.

EXAMPLE 9

Preparation of a Boron Silicate of the MCM-41 Structure 156.7 g of tetramethylammonium hydroxide solution (10 wt. %) is placed in a polyethylene beaker and 42.3 g of pyrogenic silicon-boron mixed oxide containing 5.5 wt. % of $B_2O_3$ is added, with stirring. This mixture is stirred for one hour. A suspension of 65.5 g of cetyltrimethylammonium bromide $(C_{16}H_{33}(CH_3)_3NBr)$ in 576.5 g of deionized water is then added, with stirring, and stirring is continued for 10 minutes. The pH is adjusted to 11.5 by the addition of dilute sulphuric acid. The resulting synthesis gel is crystallized in an autoclave for 48 hours at 140° C. under static conditions. The solid obtained is filtered off and washed with deionized water until the filtrate is neutral. The solid is dried to 90° C. and then calcined in an air atmosphere for four hours at 540° C.

The X-ray diffraction diagram of the catalyst obtained shows the diffraction pattern typical of the MCM-41 materials. Examination by sorption analysis with nitrogen at 77° K shows a mean pore diameter of 2.83 nm, a BET specific surface area of 1060 m²/g and a pore volume of 0.89 ml/g.

EXAMPLE 10

Preparation of a Zirconium Silicalite-1 Powder 62.4 g of tetrapropylammonium hydroxide solution (40 wt. %) and 229.8 g of deionized water are placed in a polyethylene beaker and 57.4 g of pyrogenic silicon-zirconium oxide containing 3.0 wt. % of $ZrO_2$ are added, with stirring. The resulting synthesis gel is then crystallized in an autoclave for 24 hours at 175° C. The solid obtained is separated from the mother liquor by centrifugation, washed with three times 250 ml of deionized water, dried at 90° C. and calcined in an air atmosphere for four hours at 550° C.

The X-ray diffraction diagram of the catalyst obtained shows the diffraction pattern typical of the MFI structure. X-ray fluorescence analysis gives $ZrO_2$ content of 1.0 wt. %

EXAMPLE 11

Preparation of a Zirconium Silicate of the MCM-41 Structure 114.2 g of tetramethylammonium hydroxide solution (10 wt. %) are placed in a polyethylene beaker and 30.0 g of pyrogenic silicon-zirconium oxide containing 3.0 wt. % of $ZrO_2$ is added, with stirring. This mixture is stirred for one hour. A suspension of 29.1 g of cetyltrimethylammonium bromide $(C_{16}H_{33}(CH_3)_3NBr)$ in 109.2 g of deionized water is then added, with stirring, and stirring is continued for 10 minutes. The resulting synthesis gel is crystallized in an autoclave for 48 hours at 140° C. under static conditions. The solid obtained is filtered off and washed with deionized water until the filtrate is neutral. The solid is dried to 90° C. and then calcined in an air atmosphere for four hours at 640° C.

The X-ray diffraction diagram of the catalyst obtained shows the diffraction pattern typical of the MCM-41 materials with a $d_{100}$ value of 3.25 nm. Examination by sorption analysis with nitrogen at 77 K shows a mean pore diameter of 2.4 nm, a BET specific surface area of 860 m²/g and a pore volume of 0.59 ml/g.

Further variations and modifications of the foregoing will be apparent to those skilled in the art and intended to be encompassed by the claims appended hereto.

German priority application 196 24 340.8 is relied on and incorporated hereby reference.

We claim:

1. A process for the preparation of microporous and mesoporous metal silicates, comprising the hydrothermal reaction of a silicon and metal source in the presence of a template, wherein a pyrogenic metal-silicon mixed oxide is used as the silicon and metal source.

2. The process according to claim 1 for the preparation of crystalline microporous and mesoporous metal silicates of the general composition $$(SiO_2)_{1-x}(A_mO_n)_x \qquad (Ia),$$

$$(SiO_2)_{1-x}((A_mO_n)_{1-y}(A'_{m'}O_{n'})_y)_x \qquad (Ib)$$

or $$(SiO_2)_{1-x}(M_rA_mO_{n''})_x \qquad (II)$$

in which x is a number from 0.0001 to 0.25;

y is a number greater than 0 and less than 1;

A and A' are a metal of valency p selected from the group consisting of B, Al, Ga, In, Ge, Sn, Pb and subgroups 3 to 8;

M is a cation of valency q selected from the group consisting of alkali metals, alkaline earth metals, $H^+$, $NH_4^+$ and $N(alkyl)_4^+$ m, m', n, n', n" and r are the number of atoms, where:

$$m \cdot p = 2n \text{ and } m' \cdot p = 2n' \text{ and}$$

$$m \cdot P + r \cdot q = 2n'',$$

wherein said pyrogenic mixed oxide has the composition of formula (Ia) or (Ib) and the cation M of formula (II) is incorporated via the template or via alkali metal or alkaline earth metal hydroxide present in the hydrothermal reaction.

3. The process according to claim 1 wherein said pyrogenic metal-silicon mixed oxide is prepared by flame hydrolysis.

4. The process according to claim 1 wherein said pyrogenic mixed oxide is selected from the group consisting of $(SiO_2)_{1-x}(TiO_2)_x$, $(SiO_2)_{1-x}(Al_2O_3)_x$, $(SiO_2)_{1-x}(B_2O_3)_x$, $(SiO_2)_{1-x}(V_2O_5)_x$ and $(SiO_2)_{1-x}(ZrO_2)_x$, in which x is 0.0001 to 0.25.

5. The process according to claim 1 wherein said template is an amine having one or more amino groups, an amino alcohol or a tetrasubstituted ammonium compound.

6. The process according to claim 1 wherein said template is tetraalkylammonium.

7. The process according to claim 1 wherein said template is used in an amount of 0.05 to 2.0 mol per mol of $SiO_2$ in the mixed oxide.

8. The process according to claim 1 further comprising that the hydrothermal reaction in the preparation of microporous metal silicates is carried out at a temperature from 100 to 220° C.

9. The process according to claim 1 further comprising that the hydrothermal reaction in the preparation of microporous metal silicates is carried out at a temperature from 150 to 190° C.

10. The process according to claim 1 wherein the preparation of mesoporous metal silicates is carried out at a temperature from 50 to 175° C. under at least autogenous pressure.

11. The process according to claim 1 wherein the preparation of mesoporous metal silicates is carried out at a temperature from 70 to 150° C. under at least autogenous pressure.

12. The process according to claim 1, wherein the pyrogenic mixed oxide is brought into contact with an aqueous solution containing hydroxyl ions and said template, the molar ratio of $OH^-$ to $SiO_2$ being from 0.05 to 2.0.

13. The process according to claim 1 wherein said template compound is removed from the hydrothermal reaction by calcining from 300 to 1000° C.

14. The process according to claim 1 wherein the pyrogenic metal-silicon mixed oxide is used in the form of a shaped object, the size and shape of the shaped objects remaining essentially unchanged in the hydrothermal reaction to give microporous and mesoporous metal silicates.

15. The process according to claim 14 wherein said pyrogenic metal-silicon mixed oxide is pore free.

16. The process according to claim 6 wherein said template is selected from the group consisting of tetraethylammonium hydroxide, tetra-n-propylammonium hydroxide and tetra-n-butylammonium hydroxide, and a microporous metal silicate with MFI, MEL or BEA structure is formed.

17. The process according to claim 6 wherein a template of structure $RNR'_3{}^+X^-$ is used in which R stands for an alkyl group with at least 7 carbon atoms, R' stands for methyl or ethyl and X stands for hydroxide or a halide, and a mesoporous metal silicate with MCM-41 or MCM-48 structure is formed.

18. The process according to claim 14 wherein the shaped objects are formed by spray drying of a suspension consisting of the pyrogenic silicon metal mixed oxide and an aqueous solution of the template.

19. A process for the preparation of crystalline microporous titanium silicates of the general composition $(SiO_2)_{1-x}(TiO_2)_x$ in which x is a number from 0.001 to 0.2 wherein a pyrogenic silicon-titanium mixed oxide is reacted with a tetraalkylammonium hydroxide template in a hydrothermal reaction at a temperature from 100 to 220° C.

20. The process of claim 19, wherein the pyrogenic silicon-titanium mixed oxide is shaped to microgranules by a spray drying process prior to the hydrothermal reaction and a crystalline microporous titanium silicate in the form at microgranules is formed.

* * * * *